United States Patent
Yeh et al.

(10) Patent No.: US 10,316,283 B2
(45) Date of Patent: Jun. 11, 2019

(54) CONCENTRICALLY BAFFLED REACTORS AND SYSTEMS THAT INCORPORATE THEM

(71) Applicant: UNIVERSITY OF SOUTH FLORIDA, Tampa, FL (US)

(72) Inventors: Daniel H. Yeh, Tampa, FL (US); Onur Y. Ozcan, Tampa, FL (US); Robert A. Bair, Tampa, FL (US)

(73) Assignee: University of South Florida, Tampa, FL (US)

( * ) Notice: Subject to any disclaimer, the term of this patent is extended or adjusted under 35 U.S.C. 154(b) by 290 days.

(21) Appl. No.: 15/122,967

(22) PCT Filed: Mar. 3, 2015

(86) PCT No.: PCT/US2015/018495
§ 371 (c)(1),
(2) Date: Sep. 1, 2016

(87) PCT Pub. No.: WO2015/134501
PCT Pub. Date: Sep. 11, 2015

(65) Prior Publication Data
US 2017/0067005 A1  Mar. 9, 2017

Related U.S. Application Data

(60) Provisional application No. 61/947,664, filed on Mar. 4, 2014.

(51) Int. Cl.
*B01D 21/00* (2006.01)
*B01D 21/24* (2006.01)
(Continued)

(52) U.S. Cl.
CPC ........... *C12M 27/20* (2013.01); *B01D 21/003* (2013.01); *B01D 21/0042* (2013.01);
(Continued)

(58) Field of Classification Search
CPC ...... B01J 19/006; B01J 19/244; C02F 1/5281; C12M 23/34; C12M 27/20; C12M 29/04;
(Continued)

(56) References Cited

U.S. PATENT DOCUMENTS 2,413,375 A * 12/1946 Pomeroy ............... B01D 17/041
366/182.4
3,881,700 A * 5/1975 Bradford ............... C02F 1/5236
210/207

(Continued)

FOREIGN PATENT DOCUMENTS

WO  WO-9404466 A1 * 3/1994  ............ C02F 1/5281

OTHER PUBLICATIONS

Ozcan, Onur, "Development of an Anaerobic-Phototrophic Bioreactor System for Wastewater Treatment", A dissertation submitted in partial fulfillment of the requirements for the degree of Doctor of Philosophy, 2016.

*Primary Examiner* — Lucas A Stelling
(74) *Attorney, Agent, or Firm* — Thomas | Horstemeyer, LLP

(57) ABSTRACT

In one embodiment, a concentrically baffled reactor includes an outer housing that defines an interior space, an inlet through which material can be delivered into the interior space, an outlet through which material can be removed from the interior space, and multiple concentric baffles within the interior space that define multiple concentric reactor zones through which the material can sequentially flow to the outlet.

10 Claims, 12 Drawing Sheets

(51) Int. Cl.
 *B01J 19/00* (2006.01)
 *C02F 1/52* (2006.01)
 *C12M 1/00* (2006.01)
(52) U.S. Cl.
 CPC ..... *B01D 21/0045* (2013.01); *B01D 21/0066* (2013.01); *B01D 21/245* (2013.01); *B01J 19/006* (2013.01); *C02F 1/5281* (2013.01); *C12M 23/34* (2013.01); *C12M 29/04* (2013.01); *C12M 29/18* (2013.01); *C12M 41/14* (2013.01)
(58) Field of Classification Search
 CPC ..... C12M 29/18; C12M 41/14; B01D 21/003; B01D 21/0039; B01D 21/0042; B01D 21/0045; B01D 21/0051; B01D 21/0066; B01D 21/2427; B01D 21/245; B01D 24/007; B01D 24/008; B01D 24/18
 See application file for complete search history.

(56) References Cited

U.S. PATENT DOCUMENTS

| | | | | |
|---|---|---|---|---|
| 4,425,239 | A | * | 1/1984 | Jacocks .............. B01D 17/0208 210/787 |
| 6,086,765 | A | | 7/2000 | Ewards |
| 8,642,326 | B1 | * | 2/2014 | Schaefer ................ A01G 33/00 435/292.1 |
| 2006/0201861 | A1 | * | 9/2006 | Young .................. B01D 21/003 210/176 |
| 2008/0000831 | A1 | * | 1/2008 | Demergasso ........... C02F 3/345 210/609 |

\* cited by examiner

CONCENTRICALLY BAFFLED REACTORS AND SYSTEMS THAT INCORPORATE THEM

CROSS-REFERENCE TO RELATED APPLICATIONS

This application is the 35 U.S.C. § 371 national stage application of PCT Application No. PCT/US2015/018495, filed Mar. 3, 2015, which claims priority to U.S. Provisional Application Ser. No. 61/947,664, filed Mar. 4, 2014, which is hereby incorporated by reference herein in its entirety.

BACKGROUND

A reactor is an open or enclosed system with a finite volume that allows for reactions to occur inside the volume for a specific purpose. One such purpose is wastewater treatment. In current systems, wastewater treatment is often conducted in unit operations in multiple individual reactors, typically arranged in series. The reactors may have different volumes and, therefore, different hydraulic retention times (HRTs). This allows different conditions to be achieved within each reactor to facilitate optimization of the performance of the overall system.

While current systems are generally effective, they have several drawbacks. For example, the cost of fabricating each reactor can be high and the total footprint of the system can be large. In addition, it can be challenging to coordinate flow between the reactors. Furthermore, the energy required to actively pump water from reactor to reactor can be high. It would be desirable to have a reactor system that avoids some or all of these drawbacks.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have a reactor system that avoids some or all of the drawbacks associated with conventional systems. Disclosed herein are embodiments of such reactor systems. The disclosed systems incorporate one or more concentrically baffled reactors that comprise multiple concentric reactor zones that are defined by multiple concentric baffles. Feed can flow through the reactor to achieve the desired result. Domestic and industrial wastewater treatment, in which wastewater is delivered to the reactor and treated using microbes, is one application. Industrial processes, such as those used to manufacture of chemicals, enzymes, proteins, pharmaceuticals, and other products, is another application. While multiple references to wastewater treatment are made in the disclosure that follows, it is to be understood that the disclosed concentrically baffled reactors and the systems that incorporate them are not to be interpreted as being limited to any particular application or process.

A "concentrically baffled reactor" as the term is used herein is a generally cylindrical reactor having a series of concentric, generally cylindrical baffles that define separate generally cylindrical volumes or "zones" in which similar or dissimilar reactions can occur in sequence. The reactor zones function as a series of sub-reactors that progressively increase in size (diameter), and potentially increase in volume and therefore hydraulic retention time (HRT), from its center radially outward to its perimeter. Accordingly, the functionality of multiple reactors is merged into a single reactor. In so doing, the overall footprint of the system is reduced, as are construction costs and complexity. The overall flow of water can be from the center of the reactor to the perimeter or vice versa. Within each zone, the flow is vertical, alternating between upward and downward flow as directed by the baffles. In some embodiments, the flow is passive and the reactor is therefore more energy efficient, less complex, and resilient to perturbation. Because of the design of the reactor and its different reactor zones, a gradient of conditions, such as volume, temperature, particle size, solids concentration, pH, redox, microbial population, and other parameters, can be achieved in a single reactor.

Figure 1A:
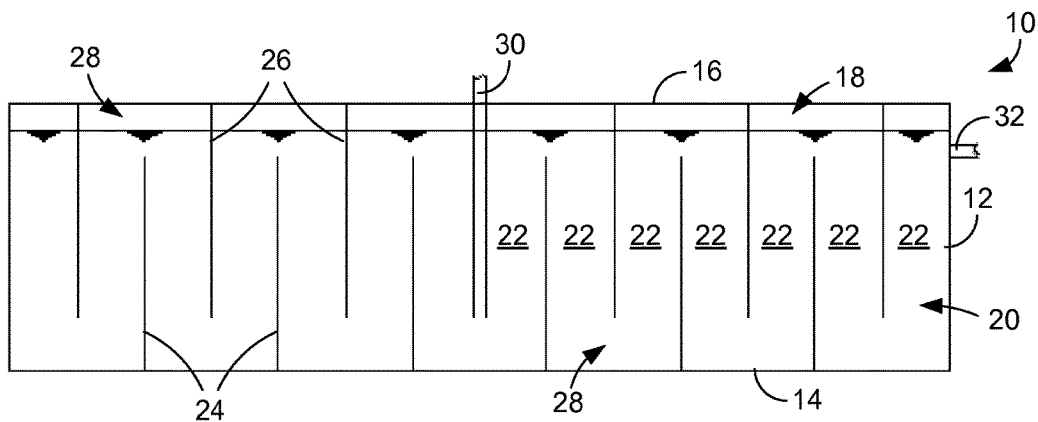
FIG. 1A is a schematic side view of a first embodiment of a concentrically baffled reactor.
Figure 1B:
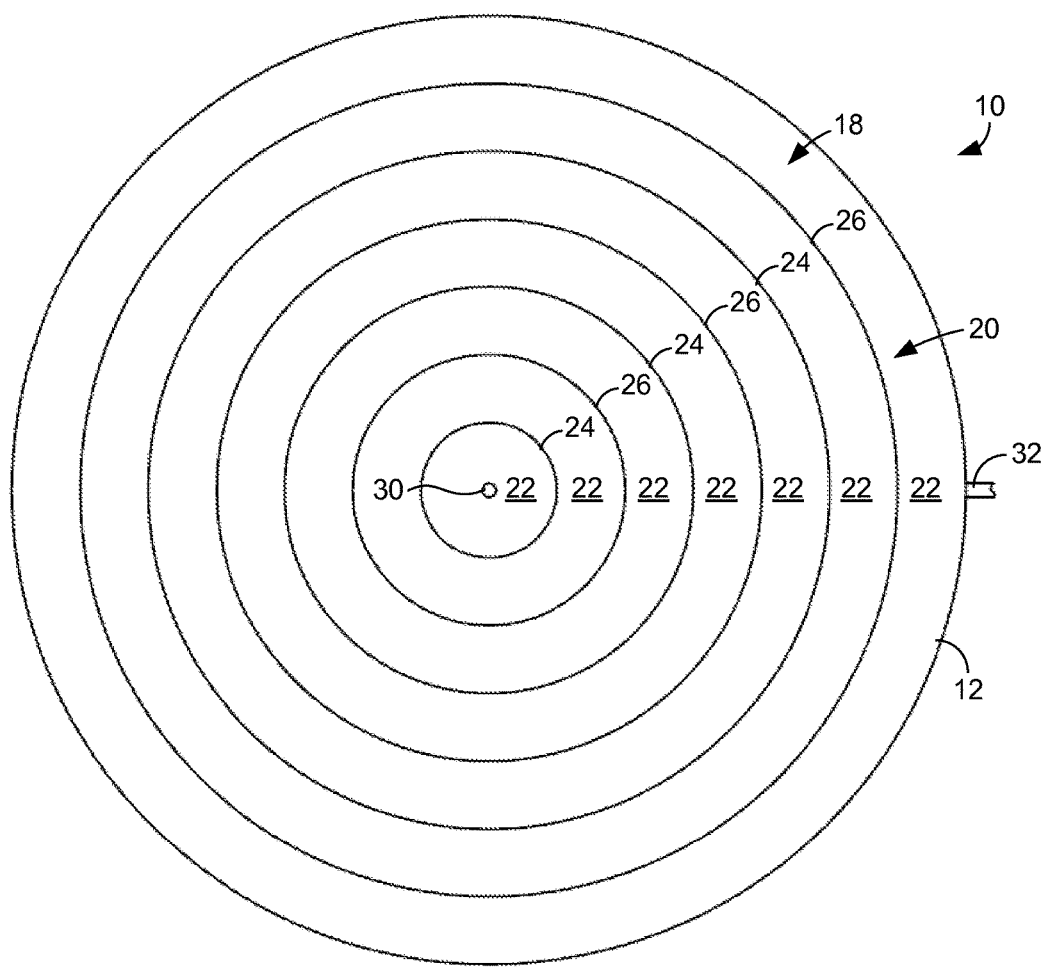
FIG. 1B is a schematic cross-sectional view of the concentrically baffled reactor of FIG. 1A.

FIGS. 1A and 1B schematically illustrate a simple example concentrically baffled reactor 10. As shown in these figures, the reactor 10 comprises a generally cylindrical housing or container that includes a generally cylindrical outer wall 12, a generally circular base 14, and a generally circular top 16 that together define an enclosed interior space 18. While the interior space 18 is enclosed, in alternative embodiments, the top of the reactor 10 can be open.

In the illustrated embodiment of FIGS. 1A and 1B, the reactor 10 has a diameter (FIG. 1B) that is significantly larger than its height (FIG. 1A). In other embodiments, however, the diameter of the reactor 10 can be the same as or smaller than the height of the reactor. When the diameter and height are substantially the same, a balance is achieved that is a compromise between settling/precipitation efficiency and reaction kinetics. Such a configuration can be used when equal parts settling/precipitation and reaction efficiency are required. Configurations in which the height of the reactor 10 is greater than its diameter may be suitable for reaction (decay/disintegration) dominated systems, rather than settling/precipitation dominated systems. Settling efficiency decreases with increasing height/diameter ratio, and reaction efficiency increases.

Provided within the interior space 18 are multiple concentric, generally cylindrical baffles 20. These baffles 20 form concentric, generally cylindrical volumes or zones 22 in which reactions can occur. In the illustrated example, the reactor 10 has six baffles 20 that together define seven such zones 22 of increasing radius and diameter (from the center to the perimeter). Of course, a greater or lesser number of baffles could be used. In the illustrated embodiment, the center reactor zone has a volume that can be described as a solid cylinder, while the outer reactor zones have volumes that can be described as hollow cylinders. As shown in FIG. 1A, the baffles 20 include lower baffles 24 that extend upward from the base 14 of the reactor 10 and upper baffles 26 that extend downward from the top 16 of the reactor. These baffles 24, 26 are arranged in an alternating configuration from the center of the reactor 10 to its perimeter. None of the baffles 20 extend all the way between the base 14 and the top 16 such that open, generally cylindrical gaps 28 are formed through which feed provided to the reactor 10 can flow from one reactor zone 22 to another in sequence.

With further reference to FIGS. 1A and 1B, the reactor 10 also includes a first line 30 that extends into and is in fluid communication with the center reactor zone and a second line 32 that is in fluid communication with the outermost reactor zone. One of these lines 30, 32 can be used as a feed inlet while the other of the lines can be used as an effluent outlet depending upon the direction in which feed is to flow through the reactor 10. As an example, feed can be delivered to the center reactor zone 22 with the line 30 and slowly flow radially outward through each reactor 10 zone until it is output from the reactor as effluent through the line 32. In the illustrated embodiment, the volume of each zone 22 increases from the center of the reactor 10 to its perimeter. This can be used to increase the HRT for the feed as it travels from the center to the perimeter of the reactor 10.

The unique geometry of a concentrically baffled reactor such as that shown in FIG. 1 increases the efficiency of reactions taking place in its finite volume due to how reaction kinetics behave in well-mixed reactors in series. A concentrically baffled reactor can perform much better than a completely stirred tank reactor (CSTR), depending on reaction kinetics and required residence times. This is due to the fact that CSTRs arranged in series approach ideal plug flow conditions as the number of discrete reaction volumes increases. Assuming a first degree reaction, the rate of consumption of a single reactant can be expressed as given in Equation 1:

$$C = \frac{C_0}{1 + kt} \quad \text{(Equation 1)}$$

where C is the remaining reactant concentration, $C_0$ is the starting reactant concentration, k is the reaction rate constant, and t is the residence time.

As the number of reactors increases for a given finite volume, the equation will be as follows:

$$C = \frac{C_0}{(1 + kt)^n} \quad \text{(Equation 2)}$$

where n is the number of equal volume reactors, and n approaches infinity.

The unique geometry of the concentrically baffled reactor also facilitates the growth of different microorganisms along the path of the incoming wastewater, which can potentially degrade the wastewater in different ways, leading to the degradation of otherwise refractory organics when a conventional system is used. Combined with temperature phasing, it is entirely possible to cultivate different classes of microorganisms in different reactor zones, leading to highly specialized microbial ecologies and varying reaction rates due to the effect of temperature on reaction kinetics within each compartment. The processes occurring within the concentrically baffled reactor under these conditions can include disintegration, hydrolysis, fermentation, and degradation, and the physical, biological, and chemical conversion of the contents of the feed wastewater to any number of products that can include water, methane, hydrogen, carbon dioxide, nutrients, and biosolids (sludge).

Figure 2:
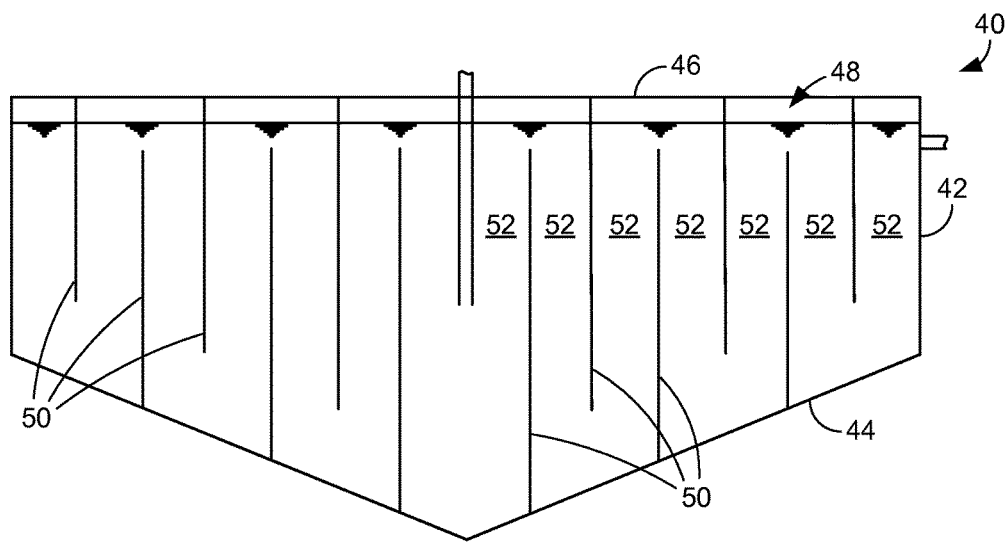
FIG. 2 is a schematic side view of a second embodiment of a concentrically baffled reactor.

As noted above, the volume of the reactor zones 22 of the reactor 10 shown in FIGS. 1A and 1B increases from the center to the perimeter of the reactor. However, the volume and volume ratios of the reactor zones 22 can altered by changing the spacing between the baffles 20. In some embodiments, the baffle spacing can be variable so that the volumes can be adjusted as needed. The reactor zone volumes can also be altered in other ways. One such way is illustrated in FIG. 2. As shown in this figure a concentrically baffled reactor 40 has a configuration that is similar to that of the reactor 10. Accordingly, the reactor 40 comprises a generally cylindrical outer wall 42, a base 44, and a generally circular top 46 that together define an enclosed interior space 48. Provided within the interior space 58 are concentric, generally cylindrical baffles 50 that extend from the base 44 and top 46 of the reactor 10. The baffles 50 form concentric, generally cylindrical reactor zones 52 in which reactions can occur. In this embodiment, however, the base 44 is conical such that the height of the reactor zones 52 decreases from the center to the perimeter of the reactor 40. In such a case, the volume of the inner zones can be increased relative to the outer zones. Alternatively, the angling of the base 44 can enable both the volumes of the inner zones 52 and the distance between the baffles 50 to remain the same despite the increasing diameter from the center to the perimeter.

It is further noted that a concentrically baffled reactor can have other geometries. For example, while the reactor shown in of FIG. 2 has a conical base, the top of the reactor could also or alternatively be conical. In addition, the base or top can have a spherical or ellipsoidal shape (see, e.g., FIG. 5). Furthermore, while the base and the top of the reactor have been shown to have a similar dimensions (diameters) and vertical outer walls and baffles, the top end of the reactor can be larger than the bottom end of the reactor, or vice versa, which can result in the outer walls and baffles having a frustoconical conical configuration.

Figure 3:
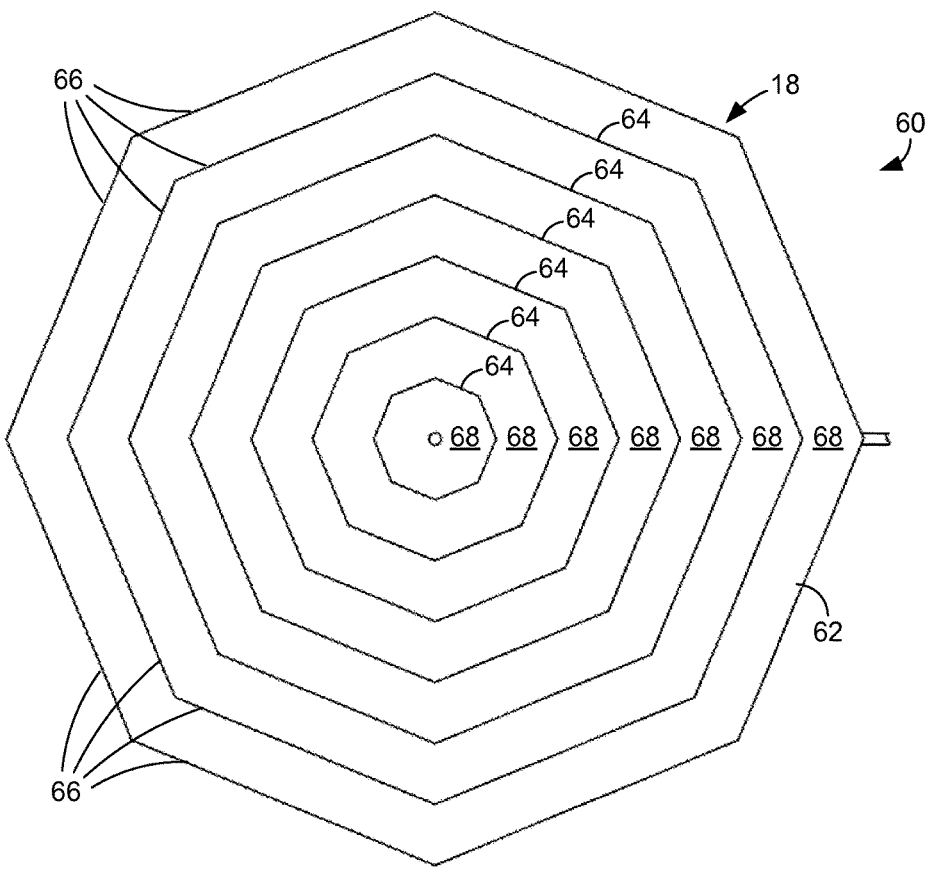
FIG. 3 is a schematic cross-sectional view of a third embodiment of a concentrically baffled reactor.

As described above a concentrically baffled reactor can be generally cylindrical and include concentric, generally cylindrical baffles. It is noted, however, that the generally cylindrical shape need not be formed by circular cylinders. Instead, the reactor and its baffles can have other shapes. For example, the cylinders may be elliptical cylinders. Alternatively, the cylinders may be polygonal cylinders, which may be easier and less expensive to manufacture or may enable several reactors to be installed more closely together to minimize footprint. FIG. 3 illustrates an example of such a concentrically baffled reactor 60. As shown in this figure, the reactor 60 comprises a generally cylindrical outer wall 62 and concentric, generally cylindrical baffles 64. Both the wall 62 and the baffles 64 are formed of multiple planar wall sections 66 that together form polygonal cylinders. In the example of FIG. 3, the outer wall 62 and the baffles 64 each have eight such wall sections 66 such that they form octagonal cylinders. Notably, other polygonal configurations are possible. In some embodiments, the outer wall and/or baffles 64 can be polygonal cylinders having at least three planar (or non-planar) wall sections.

Figure 4A:
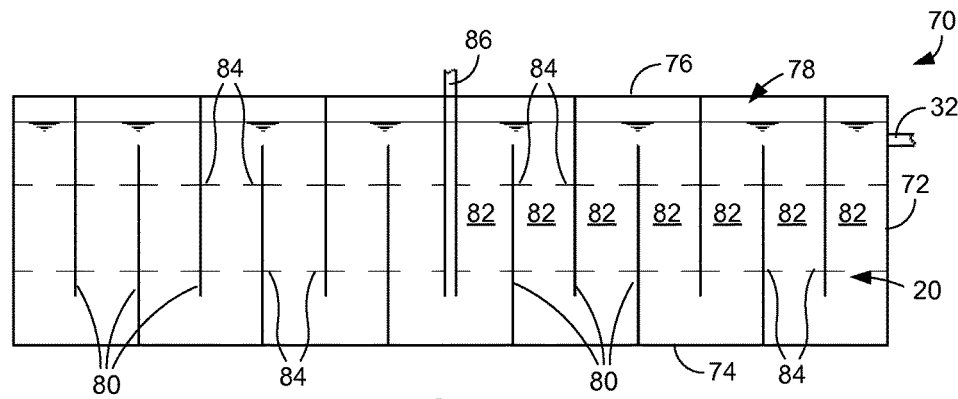
FIG. 4A is a schematic side view of a fourth embodiment of a concentrically baffled reactor.
Figure 4B:
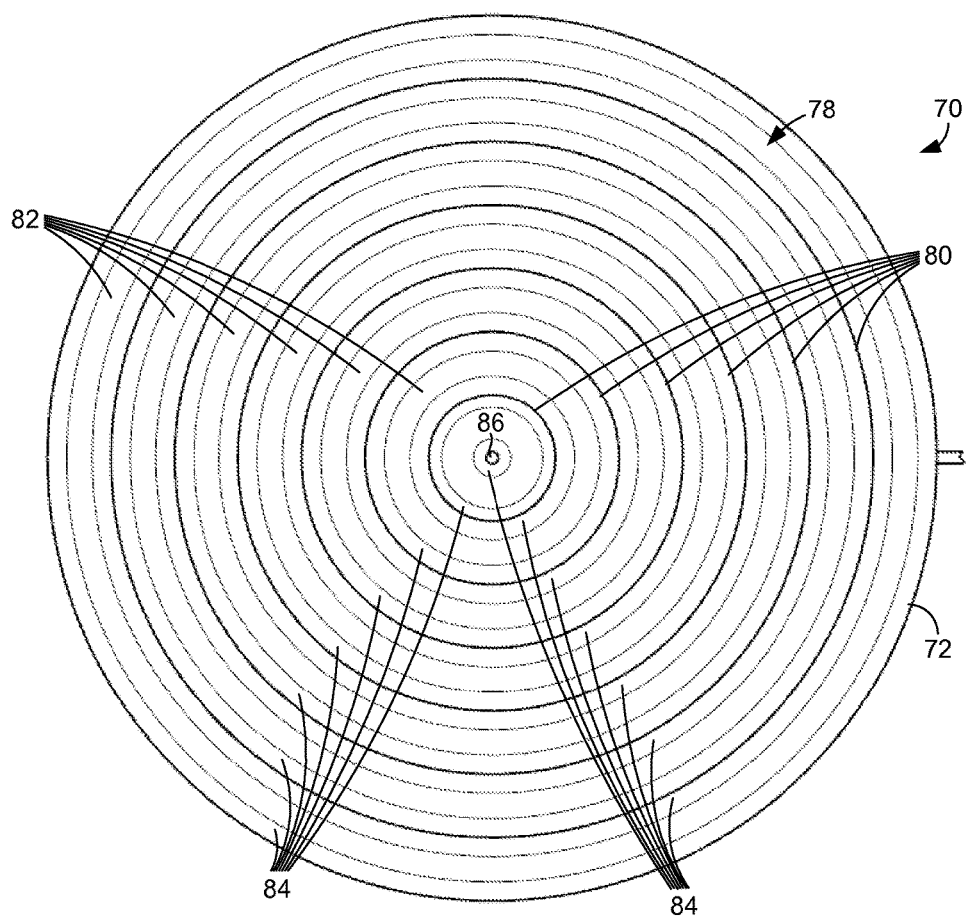
FIG. 4B is a schematic cross-sectional view of the concentrically baffled reactor of FIG. 4A.

The reactors of FIGS. 1-3 are passive reactors that do not provide for mixing other than the mixing that naturally occurs as the feed passes through the reactor from zone to zone. In other embodiments, greater mixing can be induced by the reactor. FIGS. 4-7 illustrate embodiments in which such mixing is provided. Beginning with FIGS. 4A and 4B, a concentrically baffled reactor 70 has a configuration similar to that of the reactor 10. Accordingly, the reactor 70 comprises a generally cylindrical outer wall 72, a generally circular base 74, and a generally circular top 76 that together define an enclosed interior space 78. Provided within the interior space 78 are multiple, concentric, generally cylindrical baffles 80 that form concentric, generally cylindrical reactor zones 82. In this embodiment, however, the baffles 80 are primary baffles that support generally circular secondary baffles 84 that extend laterally outward from the primary (e.g., vertical) baffles. As shown in FIG. 4B, the secondary baffles 84 can be horizontal and form concentric rings that extend either radially inward from its associated primary baffle 80 or radially outward from its associated primary baffle, as the case may be. While these secondary baffles 84 are illustrated as being horizontal in FIG. 4A, it is noted that they can form an angle with the horizontal direction so as to extend outward and either upward or downward from the primary baffles 80. In the illustrated embodiment, multiple secondary baffles 84 extend from both sides of each primary baffle 80 with a first group of the secondary baffles positioned at a first height and a second group positioned at a second height that is different from the first height so as to form two levels of secondary baffles. Of course, greater or fewer than two levels can be formed. Furthermore, in alternative embodiments, the secondary baffles 84 can be positioned at alternative heights along one or more of the reactor zones 82 so that the feed must traverse a serpentine path through the zones. As is further shown in the figures, secondary baffles 84 can also extend radially inward from the outer wall 72 and from the line 86. The secondary baffles 82 passively create eddies within the feed flow that enhance mixing of the reactants and therefore increase the efficiency of the reactor 70 or to help retain particulate matter.

Figure 5:
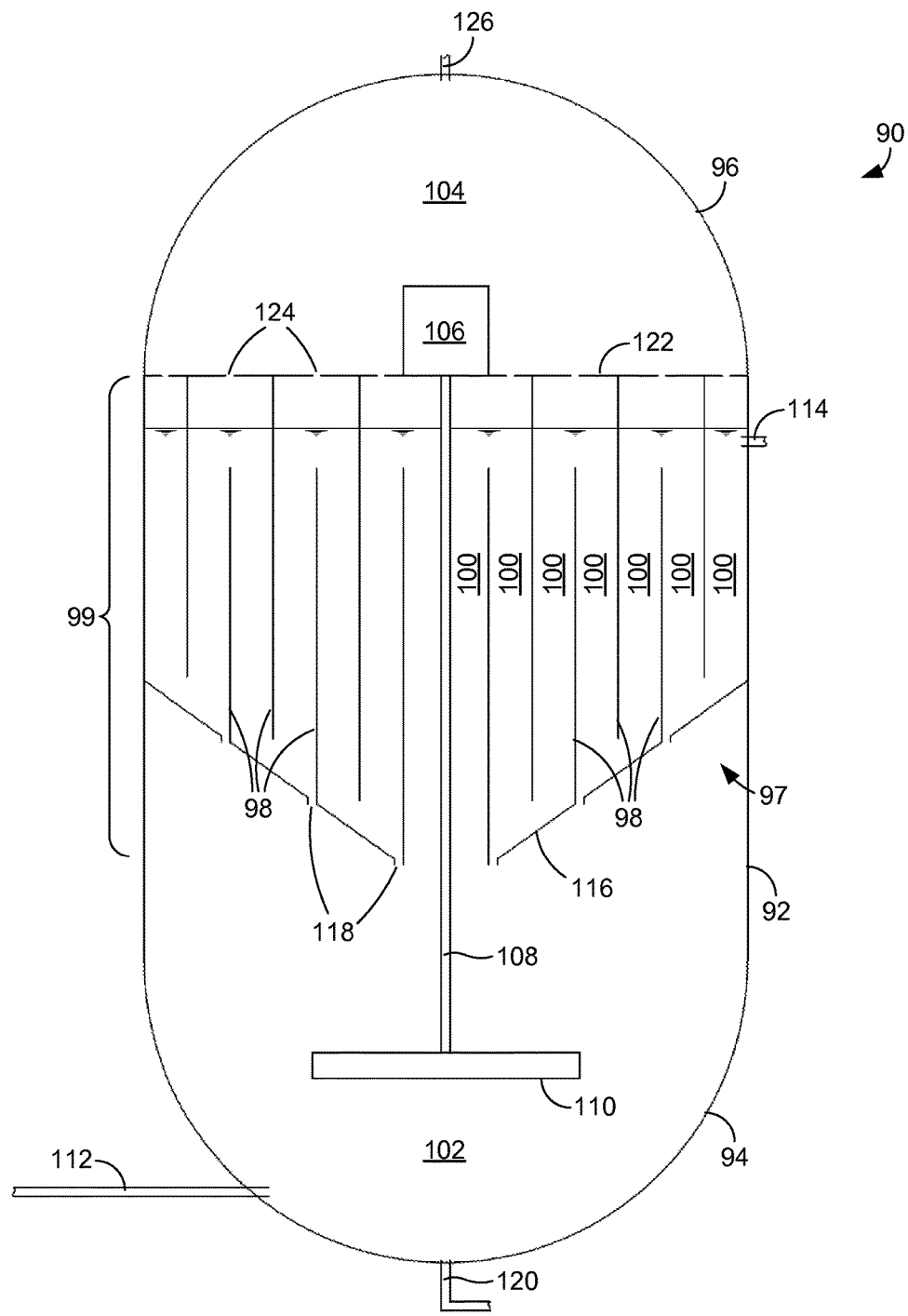
FIG. 5 is a schematic side view of a fifth embodiment of a concentrically baffled reactor.

Turning to FIG. 5, illustrated is a concentrically baffled reactor 90 that incorporates mechanical mixing. As shown in the figure, the reactor 90 comprises a container or housing having a generally cylindrical central section 92, a semispherical bottom section 94, and a semispherical top section 96 so as to have a general egg shape. In some embodiments, an existing anaerobic digester having this shape can have been retrofitted to form the concentrically baffled reactor 70.

Within the interior space 97 of the reactor 90 are concentric, generally cylindrical baffles 98 provided within a central baffle section 99 of the reactor. The baffles 98 form concentric, generally cylindrical reactor zones 100 in which reactions can occur. Positioned below the baffles 98 is a lower compartment 102 and positioned above the baffles is an upper compartment or head space 104. Positioned in the head space 104 is a motor 106 that drives a shaft 108. Mounted to a distal end of the shaft 108 is an impeller 110.

During operation of the reactor 90, feed, such as wastewater, can be delivered to the lower compartment 102 via a feed inlet 112. While in the lower compartment 102, the components of the feed can be mixed using the impeller 110. As the feed flows within the reactor 90 it eventually flows through reactor zones 100 from the center to the perimeter until reaching an effluent outlet 114 through which effluent can be passed.

In the embodiment of FIG. 5, a base 116 of the baffle section 99 is conical such that the height of the baffles 98 decreases from the center to the perimeter of the reactor 90. In addition, multiple generally circular channels 118 are formed in the base 116 that enable solids caught in the reactor zones 100 to drop down into the lower compartment 102 for mixing. A solids outlet 120 is provided at the bottom of the lower compartment 102 to enable collected solids to be removed from the reactor 90.

With further reference to FIG. 5, a top 122 of the baffle section 99 is provided with generally circular channels 124 through which biogas can escape the baffle section 99 and collect in the head space 104. This biogas can be removed from the head space using a biogas outlet 126.

Figure 6:
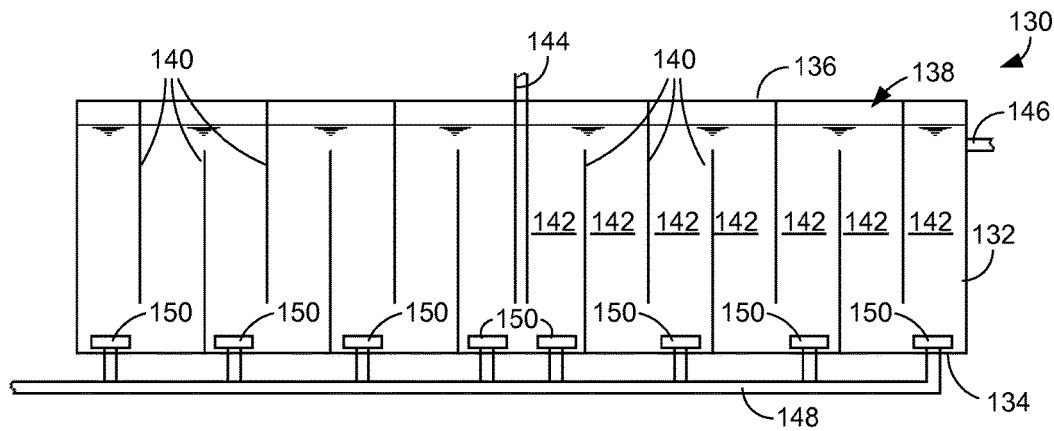
FIG. 6 is a schematic side view of a sixth embodiment of a concentrically baffled reactor.
Figure 7:
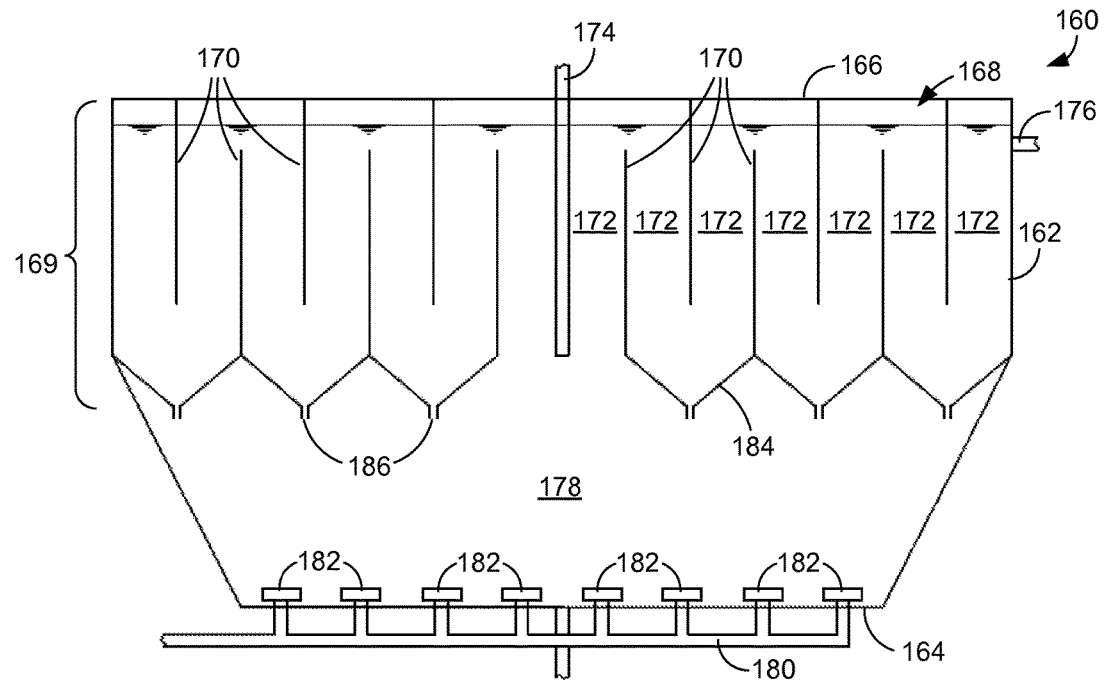
FIG. 7 is a schematic side view of a seventh embodiment of a concentrically baffled reactor.

FIGS. 6 and 7 show examples of mixing using gas bubbling. Beginning with FIG. 6, illustrated is a concentrically baffled reactor 130 that uses gas bubbling in selected reactor zones. As shown in FIG. 6, the reactor 130 comprises a generally cylindrical outer wall 132, a generally circular base 134, and a generally circular top 136 that together define an enclosed interior space 138. Provided within the interior space 138 are multiple, concentric, generally cylindrical baffles 140 that form concentric, generally cylindrical reactor or zones 142. Also provided is a feed inlet 144 and an effluent outlet 146.

As shown in the FIG. 6, the reactor 130 further comprises a gas line 148 through which gas can be delivered to selected reactor zones 142 with diffusers 150. In the illustrated embodiment, the diffusers 150 are positioned at the bottoms of reactor zones 142 through which the feed flows in the upward direction. Accordingly, the gas ejected from the diffusers 150 not only assists in mixing but further assists in driving the feed through the reactor 130 using gas lift. Furthermore, in some embodiments, the gas can assist in the reactions occurring within the reactor 130. For example, if the reactor 130 is used as an aerobic reactor, the gas can comprise air or oxygen.

Gas produced in or provided to the reactor 130 can be removed from the top end of the reactor using an appropriate gas outlet (not shown). In embodiments in which the gas input into the reactor 130 is not a reactant, biogas produced in the reactor 130 can be used as the gas ejected from the diffusers 150.

FIG. 7 illustrates a concentrically baffled reactor 160 that uses gas bubbling in a lower compartment of the reactor instead of within reactor zones. As shown in FIG. 7, the reactor 160 comprises a generally cylindrical outer wall 162, a generally circular base 164, and a generally circular top 166 that together define an interior space 168. Provided within a baffle section 169 in the interior space 168 are multiple, concentric, generally cylindrical baffles 170 that form concentric, generally cylindrical reactor zones 172. Also provided is a feed inlet 174 and an effluent outlet 176. Positioned below the baffle section 169 is a lower compartment 178 into which feed can be delivered via the feed inlet 174.

As shown in the FIG. 7, the reactor 160 further comprises a gas line 180 through which gas can be delivered to lower compartment 178 with diffusers 182. The diffusers 182 are therefore well positioned to mix solids that settle within the lower compartment 178. As before, the gas can, in some embodiments, also assist in the reactions occurring within the reactor 160.

With further reference to FIG. 7, a base 184 of the baffle section 169 includes multiple generally circular channels 186 that enable solids caught in the reactor zones 172 to drop down into the lower compartment 178 for mixing or further reaction. Gas produced in or provided to the reactor 160 can be removed from the top end of the reactor using an appropriate gas outlet (not shown).

Figure 8:
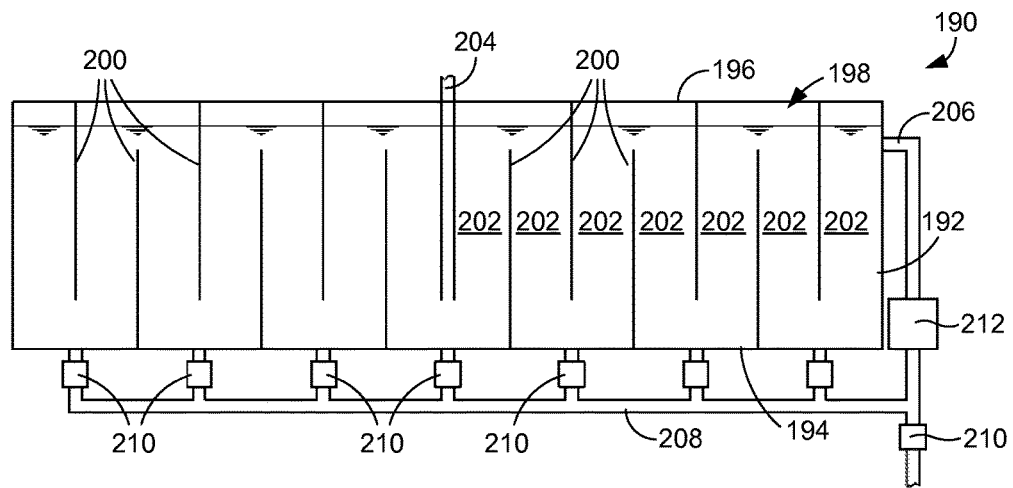
FIG. 8 is a schematic side view of an eighth embodiment of a concentrically baffled reactor.

In other embodiments, a concentrically baffled reactor can incorporate effluent recirculation. FIG. 8 illustrates an example of this. In this figure, a concentrically baffled reactor 190 comprises a generally cylindrical outer wall 192, a generally circular base 194, and a generally circular top 196 that together define an enclosed interior space 198. Provided within the interior space 198 are multiple, concentric, generally cylindrical baffles 200 that form concentric, generally cylindrical reactor zones 202. Also provided is a feed inlet 204 and an effluent outlet 206.

During operation of the reactor 190, a portion of the effluent exiting the reactor through the effluent outlet 206 is diverted into a recirculation line 208 for delivery back to the reactor zones 202. Valves 210 provided on the recirculation line 208 and the effluent outlet 206 can be used to control the flow to each individual reactor zones 202 and a pump 212 provided on the effluent outlet can be used to drive the effluent at a desired rate.

Figure 9:
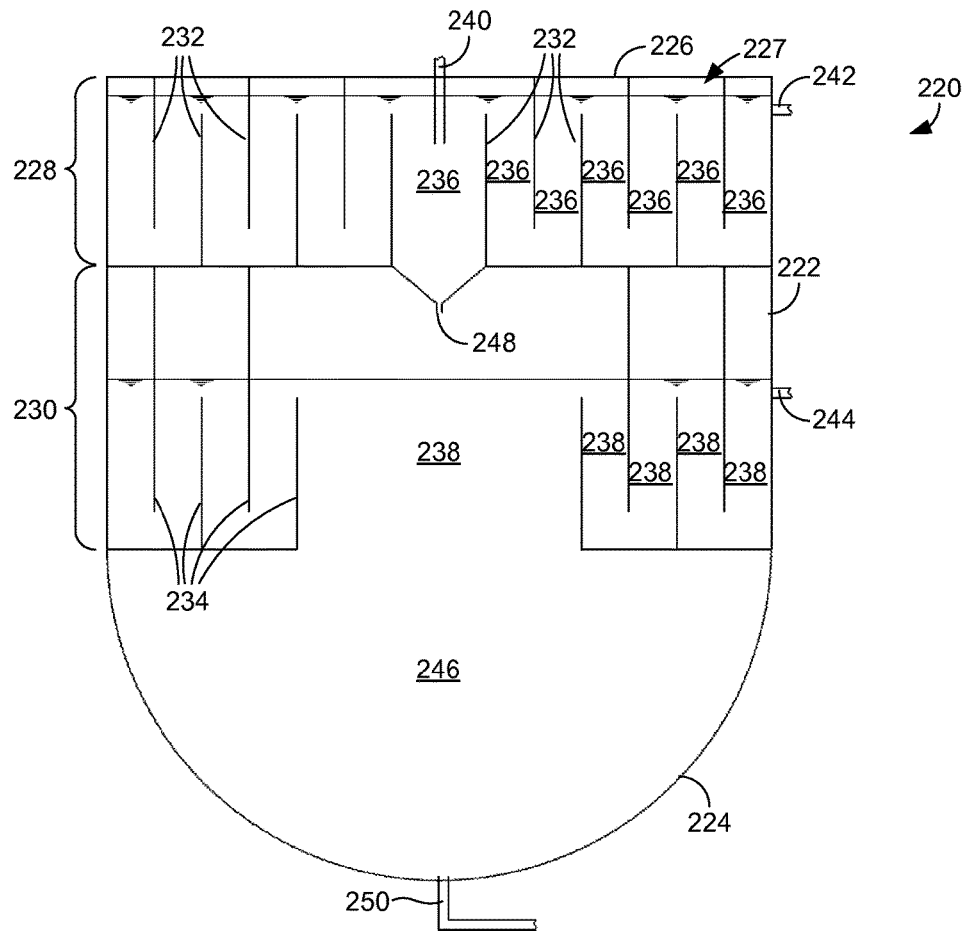
FIG. 9 is a schematic side view of a ninth embodiment of a concentrically baffled reactor.

In still other embodiments, a concentrically baffled reactor can incorporate multiple baffle sections. FIG. 9 illustrates an example of a concentrically baffled reactor 220 that incorporates two baffle sections in a stacked configuration. As shown in this figure, the reactor 220 comprises a generally cylindrical outer wall 222, a generally semispherical base 224, and a generally circular top 226 that together define an interior space 227. Provided within the interior space 227 are a first or upper baffle section 228 and a second or lower baffle section 230. These sections 228, 230 can alternatively be referred to as upper and lower concentrically baffled reactors as each has the form of an individual concentrically baffled reactor. Regardless of the terminology, each baffle section 228, 230 comprises multiple, concentric, generally cylindrical baffles 232, 234 that form concentric, generally cylindrical reactor zones 236, 238. Also provided is a feed inlet 240, a first or upper effluent outlet 242, and a second or lower effluent outlet 244. Positioned below the baffle sections 228, 230 is a lower compartment 246.

During operation of the reactor 190, feed is delivered to the central reactor zone 202 of the upper baffle section 228 and travels radially outward through the reactor zones 232 from the center to the perimeter of the section. Effluent exits the upper baffle section 228 via the upper effluent outlet 242 while feed (and particularly solids) that settles in the central reactor zone 236 drop down into the lower compartment 246 through an inner outlet 248. In similar manner to operation in the upper baffle section 228, feed travels radially outward through the reactor zones 238 of the lower baffle section 230 from the center to the perimeter of the section and effluent exits the section via the lower effluent outlet 244. Solids that collect within the lower compartment 246 can be removed through the solids outlet 250. With this configuration, the lower baffle section 230 will process feed having a greater solids concentration than the feed processed by the upper baffle section 228.

Figure 10:
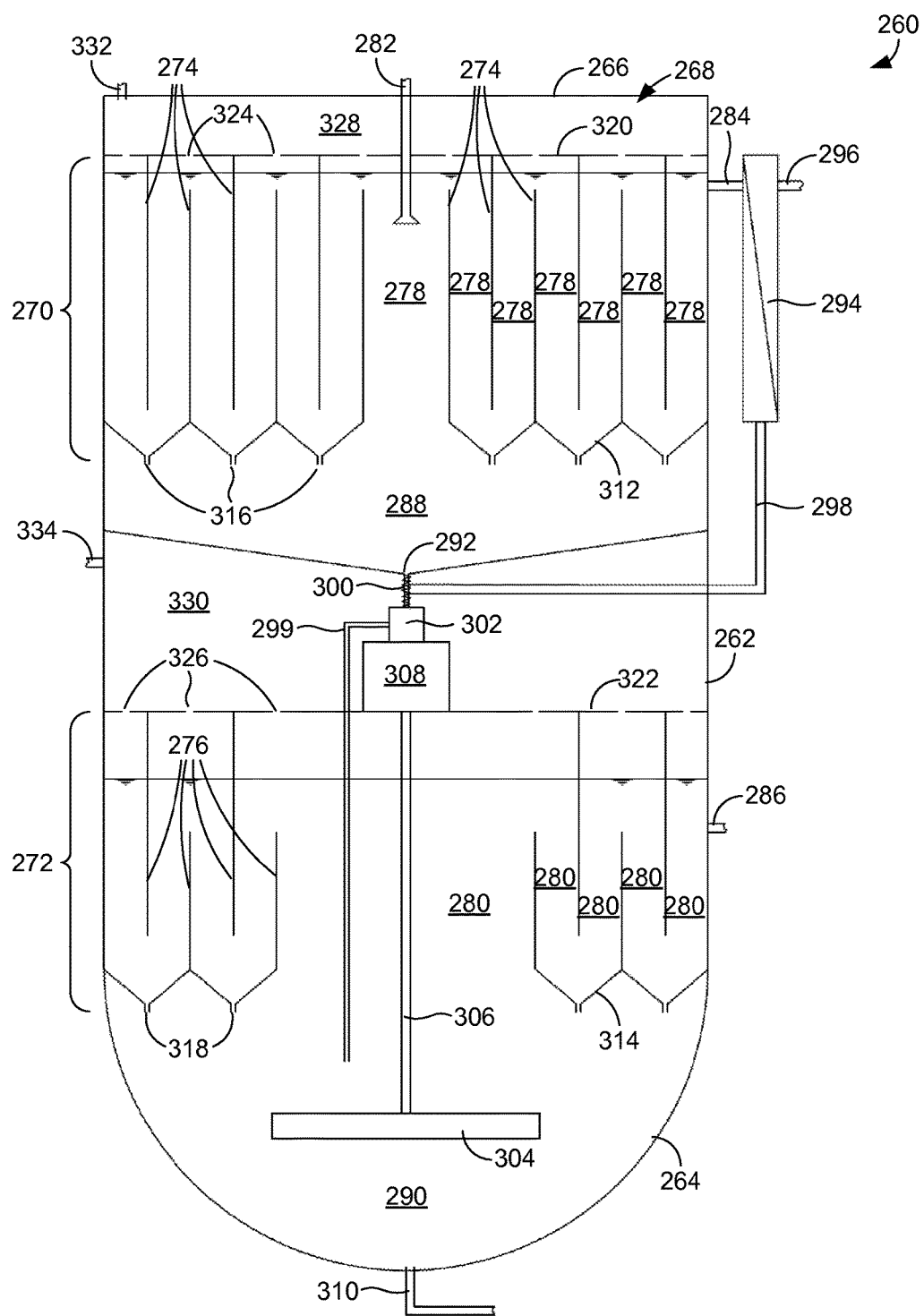
FIG. 10 is a schematic side view of a tenth embodiment of a concentrically baffled reactor.

FIG. 10 illustrates concentrically baffled reactor 260 having multiple baffle sections that can be used as an anaerobic membrane bioreactor. The reactor 260 also comprises a generally cylindrical outer wall 262, a generally semispherical base 264, and a generally circular top 266 that together define an interior space 268. Provided within the interior space 268 are a first or upper baffle section 270 and a second or lower baffle section 272. Each baffle section 270, 272 comprises multiple, concentric, generally cylindrical baffles 274, 276 that form concentric, generally cylindrical reactor zones 278, 280. Also provided is a feed inlet 282, a first or upper effluent outlet 284, and a second or lower effluent outlet 286. Positioned below the upper baffle section 270 is a first lower compartment 288 and positioned below the lower baffle section 270 is a second lower compartment 290.

During operation of the reactor 260, feed is delivered to the central reactor zone 278 of the upper baffle section 270 and travels radially outward through the reactor zones 278 from the center to the perimeter of the section. Effluent exits the upper baffle section 270 via the upper effluent outlet 284 while solids that settle in the first lower compartment 288 drop down into a solids outlet 292. The effluent passes through a membrane filtration unit 294 that filters particulate and colloidal matter from the effluent and outputs permeate through a permeate outlet 296. Remaining effluent and filtered particulate/colloidal matter then travels through a concentrate line 298 to the solids outlet 292.

With further reference to FIG. 10, a heating element 300 preheats the material passing through the solids outlet 292. Such heat can assist in the breakdown of the solids as well as destroy pathogens that they contain. After being heated, the material is driven by a pump 302 into the second lower compartment 290. There, an impeller 304 driven by a shaft 306 turned by a motor 308 mixes the material within the second lower compartment 290.

In similar manner to operation in the upper baffle section 270, feed travels radially outward through the reactor zones 280 of the lower baffle section 272 from the center to the perimeter of the section and effluent exits the section via the lower effluent outlet 286. Solids that collect within the second lower compartment 290 can be removed through the mixed liquor outlet 310.

As is further illustrated in FIG. 10, both the upper baffle section 270 and the lower baffle section 272 can be provided with a base 312, 314 having generally circular channels 316, 318 through which solids can pass. In addition, both the upper baffle section 270 and the lower baffle section 272 can be provided with a top 320, 322 that includes generally circular channels 324, 326 through which biogas can escape and collect in a head space 328, 330. This gas can be removed from the reactor 260 using biogas outlets 332, 334.

Figure 11:
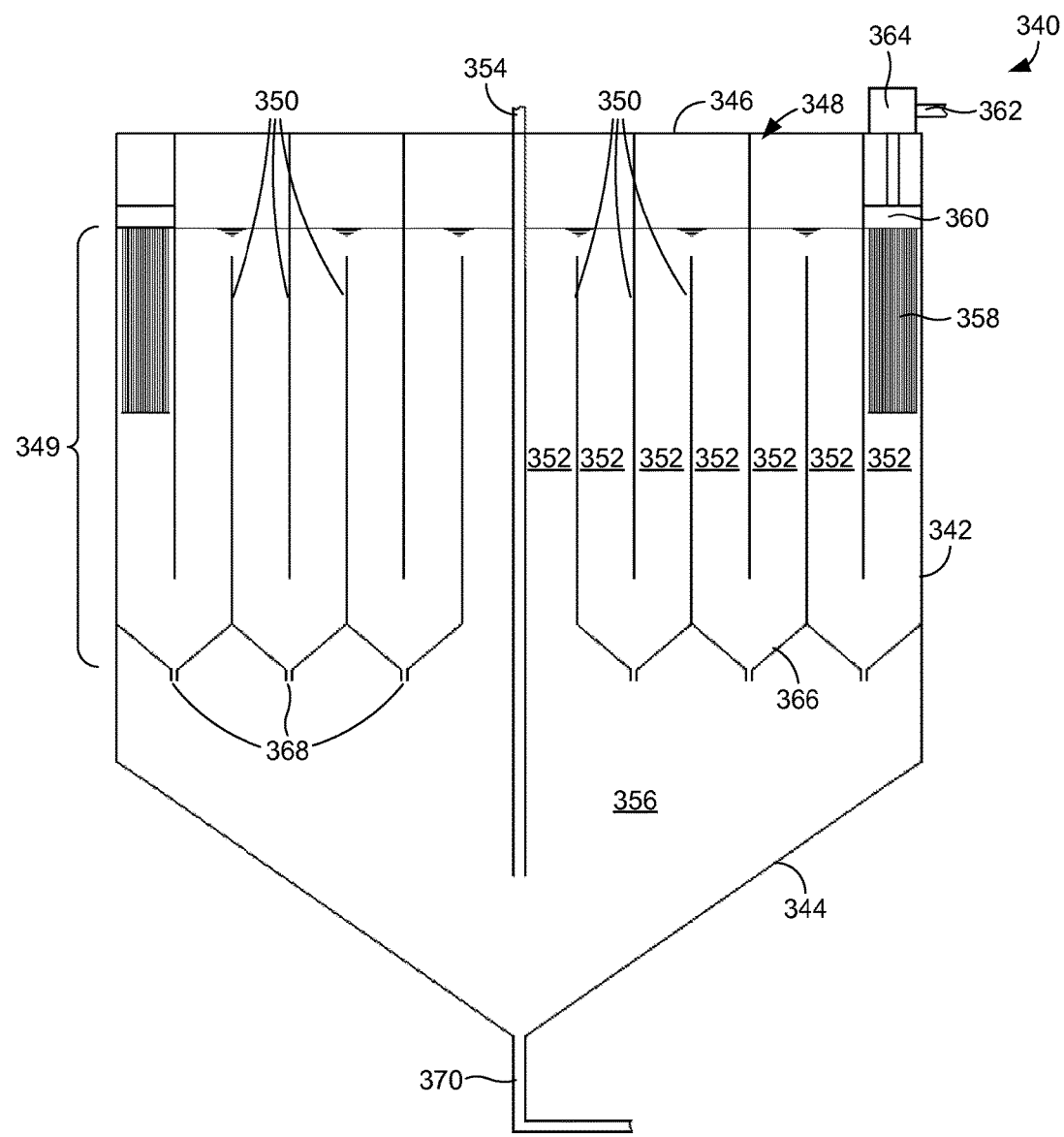
FIG. 11 is a schematic side view of an eleventh embodiment of a concentrically baffled reactor.

FIG. 11 illustrates a further concentrically baffled reactor 340 that incorporates membrane filtration. As shown in FIG. 11, the reactor 340 comprises a generally cylindrical outer wall 342, a conical base 344, and a generally circular top 346 that together define an interior space 348. Provided within a baffle section 349 of the interior space 348 are multiple, concentric, generally cylindrical baffles 350 that form concentric, generally cylindrical reactor zones 352. Also provided is a feed inlet 354. Positioned below the baffle section 349 is a lower compartment 356 into which feed can be delivered via the feed inlet 354.

As shown in the figure, provided within the outermost reactor zone 352 is a generally cylindrical membrane filter 358 that can filter particulate and colloidal matter from the effluent delivered to the outermost reactor zone to produce permeate. The permeate can be collected in a permeate collection area 360 and driven out of the reactor 340 through a permeate outlet 362 using a pump 364.

With further reference to FIG. 11, a base 366 of the baffle section 349 includes multiple generally circular channels 368 that enable solids caught in the reactor zones 352 to drop down into the lower compartment 356. Solids that collect in the lower compartment 356 can be removed via a solids outlet 370.

Figure 12A:
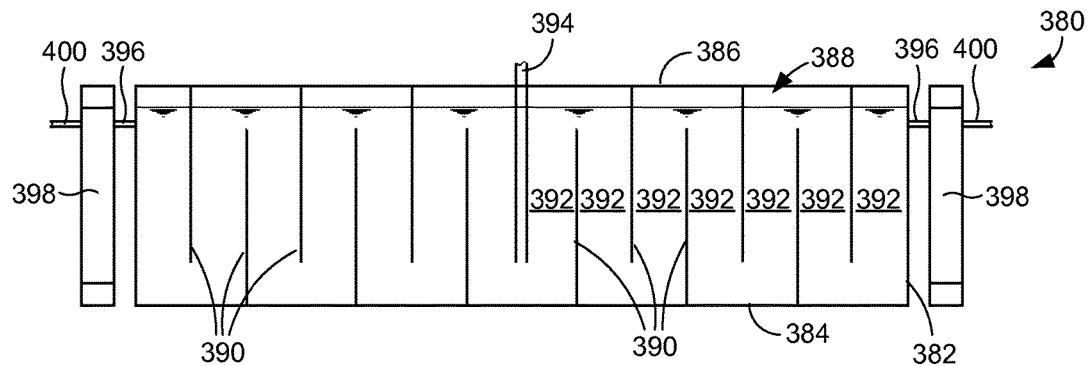
FIG. 12A is a schematic side view of a twelfth embodiment of a concentrically baffled reactor.
Figure 12B:
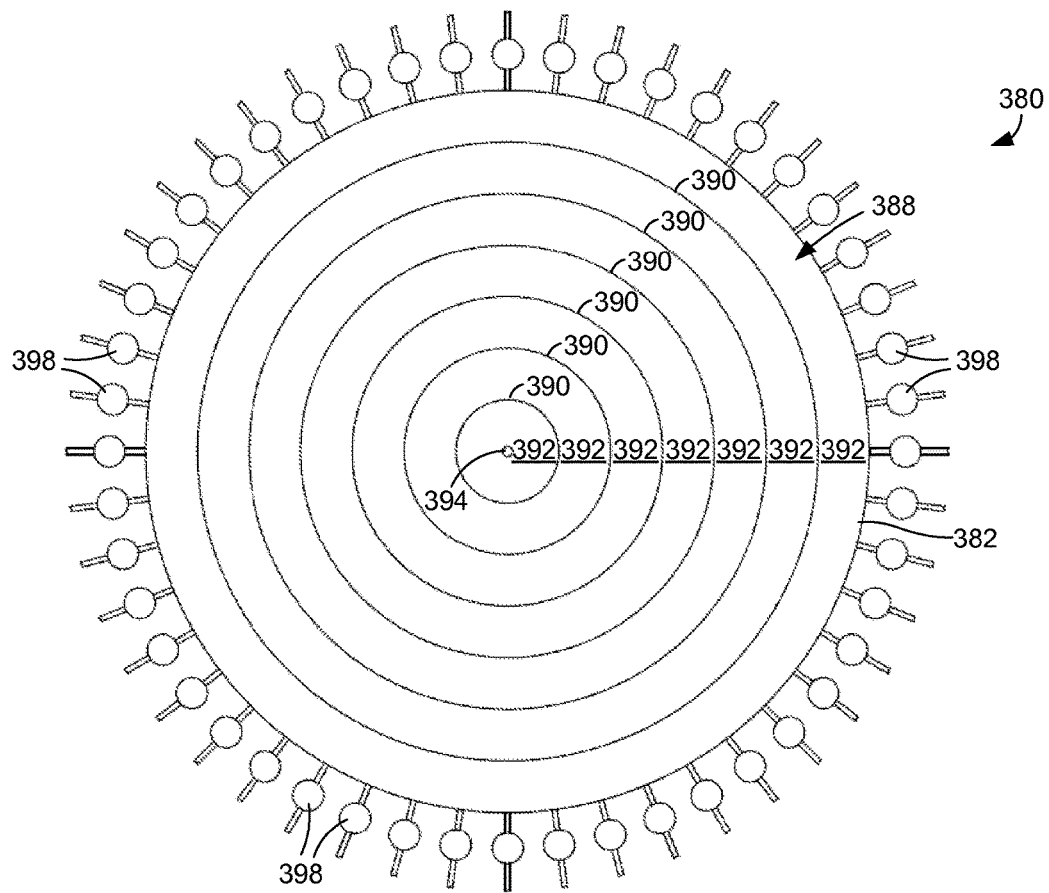
FIG. 12B is a schematic cross-sectional view of the concentrically baffled reactor of FIG. 12A.

FIGS. 12A and 12B illustrate a concentrically baffled reactor 380 that is used in conjunction with components for algae production. As shown in the figure, the reactor 380 has a configuration similar to that of the reactor 10. Accordingly, the reactor 380 comprises a generally cylindrical outer wall 382, a generally circular base 384, and a generally circular top 386 that together define an enclosed interior space 388. Provided within the interior space 388 are multiple, concentric, generally cylindrical baffles 390 that form concentric, generally cylindrical reactor zones 392. The reactor 380 further comprises a feed inlet 394 and an effluent outlet 396.

As is further shown in FIGS. 12A and 12B, each effluent outlet 396 is connected to an algae photobioreactor 398 that can be used to produce algae (e.g., microalgae) that can, for example, be used to manufacture fine chemicals, pharmaceuticals, neutraceuticals, biofuels, bioplastics, and the like. In addition, the algae photobioreactors 398 can "polish" the effluent by taking up nutrients and carbon dioxide. In the illustrated embodiment, the algae photobioreactors 398 comprise clear cylindrical containers in which the algae is grown. In some embodiments, carbon dioxide can be delivered to the algae photobioreactors 398 using appropriate inlets (not shown). Algae can be output from the algae photobioreactors 398 via algae outlets 400.

In an alternative configuration, the multiple algae photobioreactors 398 can be combined into a single algae photobioreactor. In a further alternative configuration, one or more algae photobioreactors could be incorporated into the outermost reactor zone 392 of the reactor 380. In such a case, the outer wall 382 of the reactor 380 could be transparent.

Figure 13A:
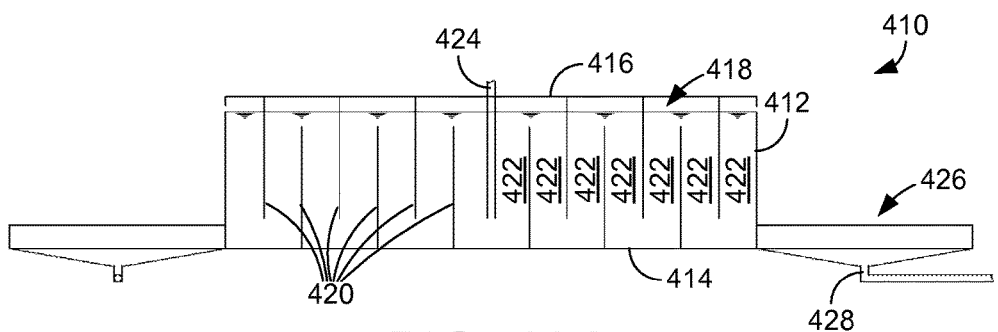
FIG. 13A is a schematic side view of a thirteenth embodiment of a concentrically baffled reactor.
Figure 13B:
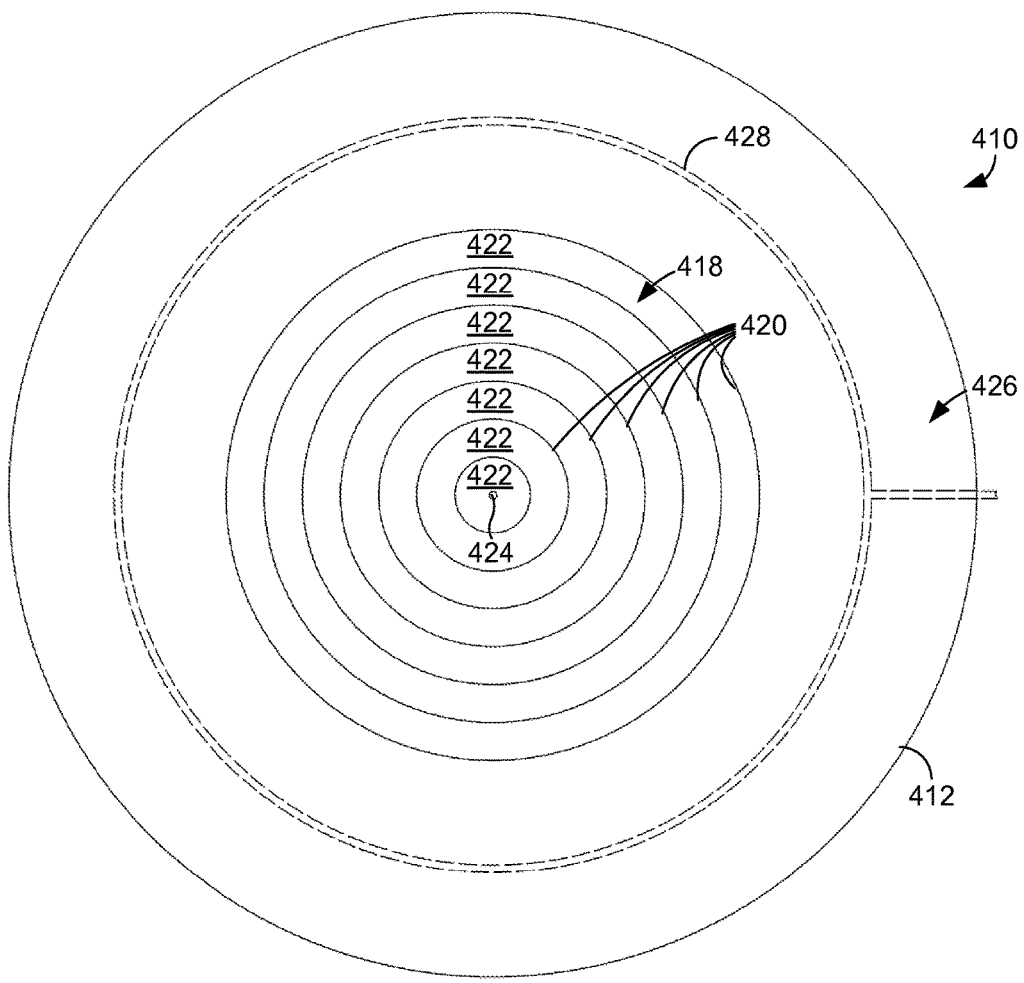
FIG. 13B is a schematic cross-sectional view of the concentrically baffled reactor of FIG. 13A.

FIGS. 13A and 13B illustrate a concentrically baffled reactor 410 that is used in conjunction with components for cultivating plants. The reactor 410 comprises a generally cylindrical outer wall 412, a generally circular base 414, and a generally circular top 416 that together define an enclosed interior space 418. Provided within the interior space 418 are multiple, concentric, generally cylindrical baffles 420 that form concentric, generally cylindrical reactor zones 422. The reactor 410 further comprises a feed inlet 424.

Effluent exiting the reactor 410 passes to a generally ring-shaped garden bed 426 that encircles the reactor in which plants can be grown. In cases in which the feed is food waste and the cultivation of the plants is cultivation of one or more food crops, the cultivation can be considered to be a form of food recycling. In some embodiments, the plant cultivation can be performed for aesthetic purposes to make the reactor 410 less conspicuous.

Figure 14A:
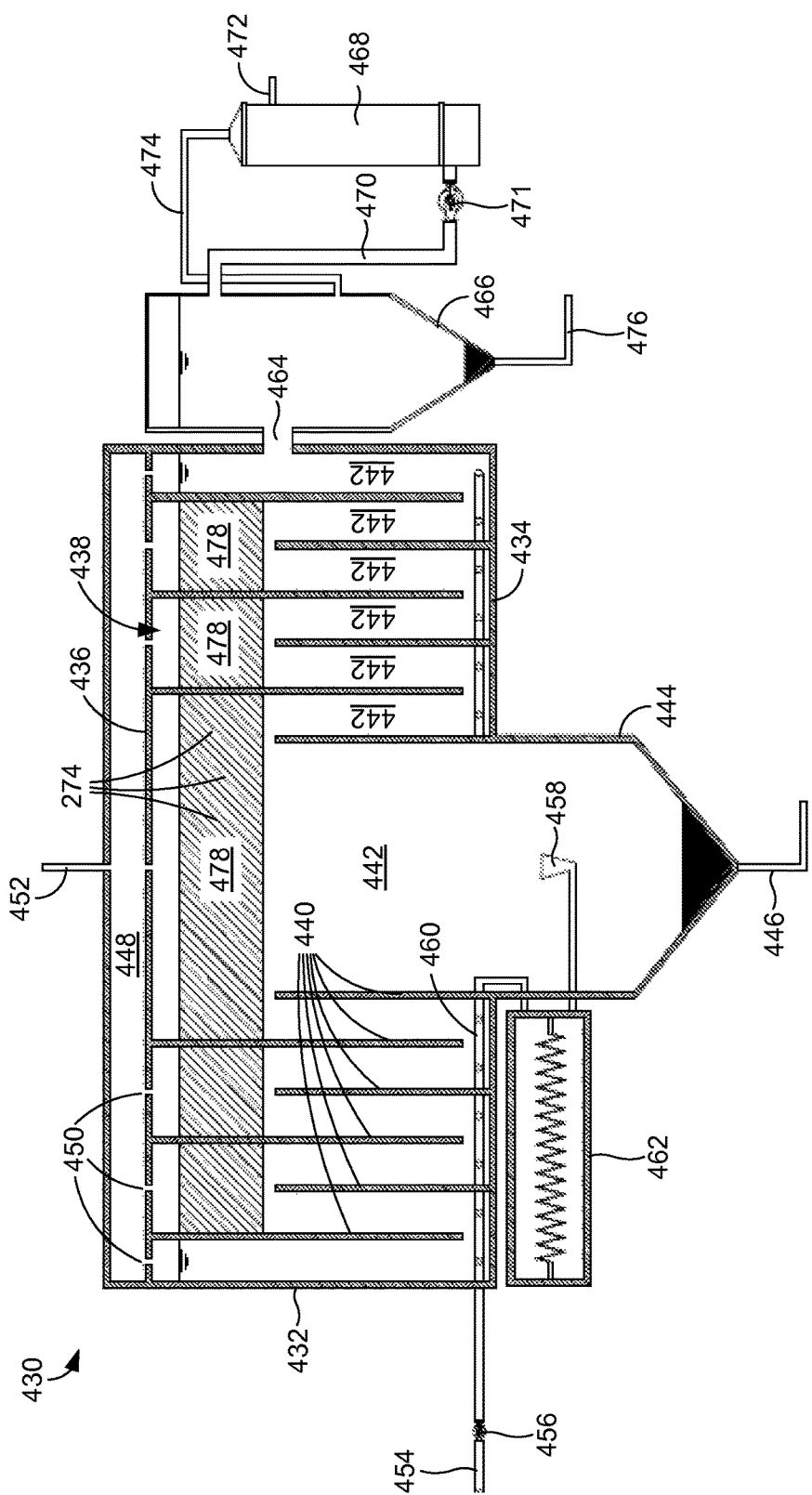
FIG. 14A is a schematic side view of a fourteenth embodiment of a concentrically baffled reactor.
Figure 14B:
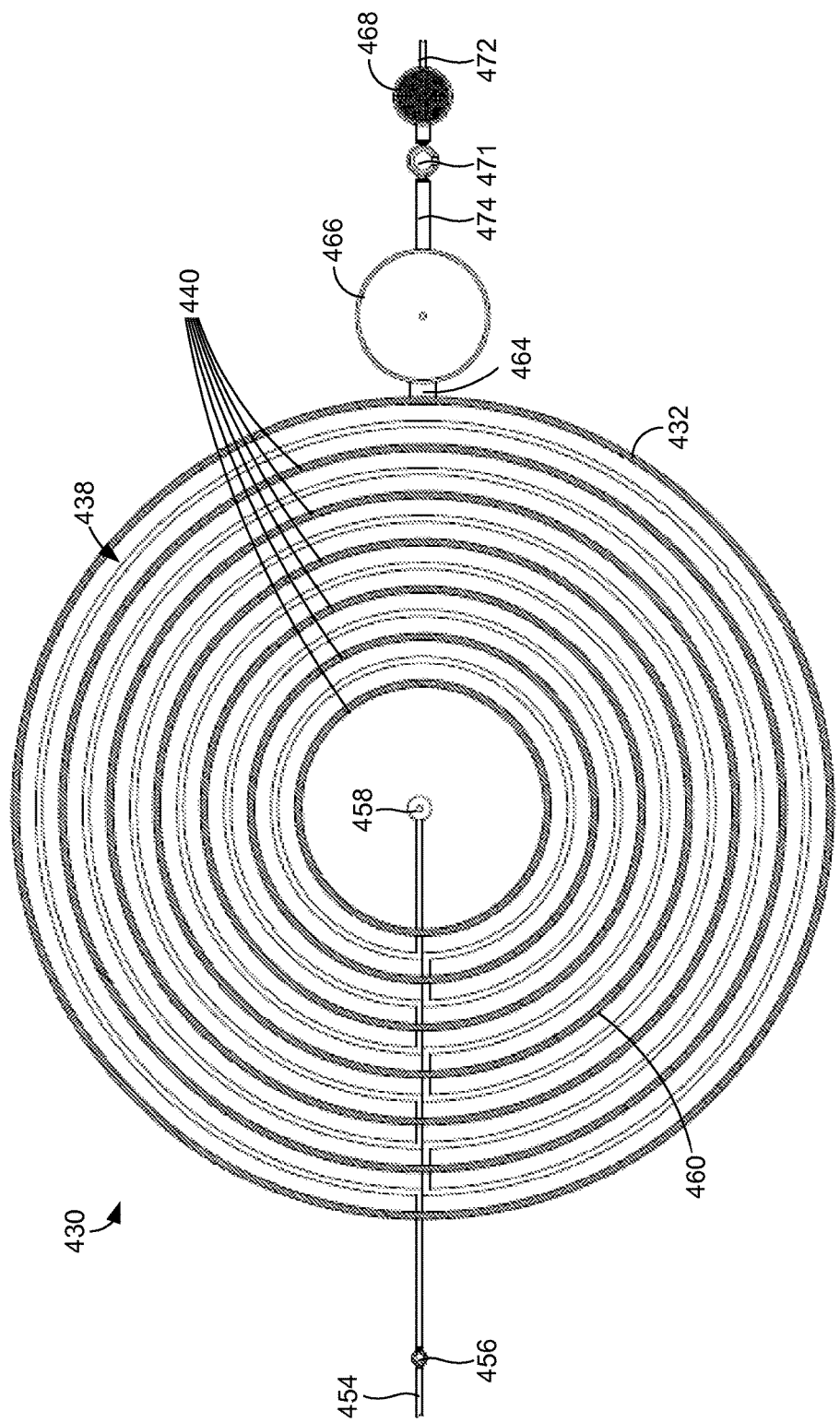
FIG. 14B is a schematic cross-sectional view of the concentrically baffled reactor of FIG. 14A.

FIGS. 14A and 14B illustrate a further concentrically baffled reactor 430 that incorporates features from other embodiments described above as well as other features. Like other embodiments, the reactor 430 comprises a generally cylindrical outer wall 432, a generally circular base 434, and a generally circular top 436 that together define an enclosed interior space 438. Provided within the interior space 438 are multiple, concentric, generally cylindrical baffles 440 that form concentric, generally cylindrical reactor zones 442. Integrated with the central reactor zone is a settlement tank 444 in which solids can settle and be removed via a solids outlet 446. The reactor 430 further includes a head space 448 in which biogas can collect after passing through generally circular channels 450 formed in the top 436. This biogas can be removed via a biogas outlet 452.

Feed is delivered to the reactor 430 with a feed inlet 454 and a pump 456. Before entering the settling tank 444 via a feed outlet 458, the feed travels through a heat exchange pipe 460 follows a serpentine path through each of the reactor zones 442 from the perimeter to the center of the reactor 430 with a section of pipe occupying each zone as shown in FIG. 14B. After traversing the heat exchange pipe 460, the feed passes through a heating chamber 462 that heats the feed before it is provided to the feed outlet 458. In some embodiments, the heating chamber 462 raises the temperature of the feed to approximately 40 to 80° C. (e.g., 55° C.). As the feed passes through the various reactor zones 442 toward the effluent outlet 464, the feed cools, thereby forming a radial thermal gradient (temperature phasing) across the reactor 430 that is highest in the center and lowest at the perimeter. The heat in the feed passing through the reactor zones 442 in turn heats the feed flowing through the heat exchange pipe 460.

The effluent exiting the reactor 430 is delivered to an external settling chamber 466 and then passes to a membrane filtration unit 468 via an effluent inlet 470 and a pump 471. The membrane filtration unit 468 filters the effluent and outputs permeate via a permeate outlet 472. Remaining effluent and filtered particulate and colloidal matter can then be returned to the settling chamber 466 via a concentrate inlet 474 and the particulate matter can settle in the settling chamber and be removed via a solids outlet 476.

As is further illustrated in FIG. 14B, floating media 478 can be provided in at least some of the reactor zones 442. This media can be porous and can, for example, be used to trap solids that float within the reactor 430 or retain reactants, such a microbes, within designated zones 442. The floating media 478 can enable a more homogeneous spatial distribution of biomass along the reactor gradient and the flow path, regardless of the velocity of the moving liquid. It is also hypothesized that the floating media will keep any floating or suspended biomass within each reactor ring from being washed out to subsequent rings. Another advantage may be in treating organic matter that floats, such as in the case of fats, oil, and grease (FOG), enabling a greater amount of microorganisms to come in contact with the substrate and speeding up its degradation.

One unique characteristic of the concentrically baffled reactor 430 is the marriage of concentric baffling with temperature phasing and heat exchange with the medium. The concentric baffling limits heat loss compared to linear rectangular designs, because the liquid moving through the reactor has considerably less contact with surfaces that can act as heat sinks to the ambient environment. The combination of heat exchange with temperature phasing is feasible from both reactor design and energy efficiency perspectives because the formation of a temperature gradient is achieved by transferring some of the heat within each concentric ring to the incoming feed, decreasing the energy required to heat the feed up to desired temperatures. Baffling itself has been shown to make anaerobic systems more resistant to hydraulic, organic, toxic shock loads than single column plug flow reactors (PFRs), which increases system robustness. Baffling has also been shown to reduce membrane fouling in anaerobic membrane reactors, which is hypothesized to be due to reduced solids concentrations and extracellular polymeric substance (EPS) production in the later compartments of the baffled reactor. Another important aspect of baffling is perhaps the prevention of biomass washout to subsequent zones, enabling the cultivation of different microbial populations along the treatment path.

Temperature phasing from thermophilic down to mesophilic and psychrophilic temperatures has the advantage of pathogen destruction within the thermophilic zone, as well as the rapid solubilization and acidification of particulates and complex molecules to be used as substrates in the subsequent zones, which increases the stability of the process by separating the acidogenesis stage of anaerobic digestion from subsequent processes. The concentrically baffled design, combined with temperature phasing will create a gradient of profiles for temperature, HRT, solids concentrations, water quality, and microbial populations along the treatment path. This change in profiles enables the waste to be subjected to different treatment conditions, and may enhance overall degradation due to a potentially broader range of enzymatic reactions involved in the process.

Various specific embodiments have been described in the preceding disclosure. It is to be understood that those embodiments are example implementations of the disclosed inventions and that alternative embodiments are possible. It is noted that such alternative embodiments can include "hybrid" embodiments that comprise one or more components or aspects from separately illustrated and described embodiments. All such alternative and/or hybrid embodiments are intended to fall within the scope of this disclosure.

The invention claimed is:

1. A concentrically baffled reactor comprising:
an outer housing that defines an interior space;
a feed inlet through which material can be delivered into the interior space;
an effluent outlet through which material can be removed from the interior space;
a concentric baffle section comprising multiple concentric baffles within the interior space that define multiple concentric reactor zones through which the material can sequentially flow to the effluent outlet, wherein the concentric baffle section includes a bottom wall that forms channels associated with the concentric reactor zones through which solids can pass from the concentric reactor zones into a lower compartment of the reactor positioned below the concentric baffle section;
a head space positioned above the concentric baffle section configured to collect biogas generated in the concentric baffle section;
a biogas outlet in fluid communication with the head space through which the biogas can exit the reactor; and
a solids outlet in fluid communication with the lower compartment through which the solids can exit the reactor.

2. The reactor of claim 1, wherein the feed inlet delivers the material to a center of the reactor, the effluent outlet removes the material from a perimeter of the reactor, and the material flows from a center reactor zone radially outward through each other reactor zone in sequence until finally passing through an outermost reactor zone.

3. The reactor of claim 1, further comprising a mechanical mixing apparatus provided within the reactor configured to mix the material within the interior space.

4. The reactor of claim 1, wherein the reactor comprises two concentric baffle sections within the interior space that are arranged in a vertically stacked configuration with an upper concentric baffle section positioned above a lower concentric baffle section, each concentric baffle section comprising multiple concentric baffles that define multiple concentric reactor zones through which the material can sequentially flow.

5. The reactor of claim 4, further comprising a heating element configured to heat the solids that pass from the upper concentric baffle section prior to the material reaching the lower concentric baffle section.

6. The reactor of claim 1, further comprising a membrane filtration unit in fluid communication with the effluent outlet, the membrane filtration unit comprising a membrane configured to filter particulate and colloidal matter from the effluent, output permeate, and return concentrate back to the interior space of the reactor.

7. The reactor of claim 3, wherein the mechanical mixing apparatus comprises an impeller provided in the lower compartment of the reactor, the impeller being mounted to a shaft that is driven by a motor.

8. The reactor of claim 5, further comprising a pump that drives the heated solids into the lower concentric baffle section.

9. The reactor of claim 1, wherein the lower wall forms an angled trough at the bottom of each concentric baffle zone, the lower channels being provided at the bottoms of the angled troughs such that the angled troughs direct solids to the lower channels.

10. A concentrically baffled reactor comprising:
an outer housing that defines an interior space;
a feed inlet configured to deliver feed to the interior space;
two concentric baffle sections provided within the interior space and arranged in a vertically stacked configuration with an upper concentric baffle section positioned above a lower concentric baffle section, wherein each concentric baffle section comprises a top wall and a bottom wall, wherein upper baffles extend down from the top wall and lower baffles extend up from the bottom wall, the upper and lower baffles being concentrically arranged with each other and alternating as the concentric baffle section is traversed from a center of the concentric baffle section to a perimeter of the concentric baffle section, wherein the upper and lower baffles define multiple concentric reactor zones through which the feed can sequentially flow, wherein the top wall forms upper channels associated with the concentric reactor zones through which biogas can escape from the concentric reactor zones and wherein the bottom wall forms lower channels associated with the concentric reactor zones through which solids can escape from the concentric reactor zones, wherein the lower wall forms an angled trough at the bottom of each concentric baffle zone, the lower channels being provided at the bottoms of the angled troughs such that the angled troughs direct solids to the lower channels;
a first effluent outlet configured to receive effluent from the upper concentric baffle section and a second effluent outlet configured to receive effluent from the lower concentric baffle section;
a first headspace positioned above the upper concentric baffle section and a second headspace positioned above the lower concentric baffle section, the headspaces being configured to collect biogas that escapes from the concentric reactor zones of their associated concentric baffle section;

a first biogas outlet associated with the first headspace and a second biogas outlet associated with the second headspace, the biogas outlets being configured to remove biogas from the headspaces;

a first lower compartment positioned below the upper concentric baffle section and a second lower compartment positioned below the lower concentric baffle section, the lower compartments being configured to collect solids that escape from the concentric reactor zones of their associated concentric baffle section;

a first solids outlet associated with the first lower compartment and a second solids outlet associated with the second lower compartment, the solids outlets being configured to remove solids from the lower compartments;

a heating element configured to heat the solids within the first solids outlet;

a pump that drives the heated solids into the second lower compartment;

a mechanical mixing apparatus comprising an impeller provided in the second lower compartment, the impeller being mounted to a shaft that is driven by a motor; and a membrane filtration unit comprising a membrane configured to filter particulate and colloidal matter from the effluent that exits the upper concentric baffle section via the first effluent outlet, to output permeate, and to return concentrate back to an inlet of the second lower compartment.

* * * * *

UNITED STATES PATENT AND TRADEMARK OFFICE
CERTIFICATE OF CORRECTION

| | |
|---|---|
| PATENT NO. | : 10,316,283 B2 |
| APPLICATION NO. | : 15/122967 |
| DATED | : June 11, 2019 |
| INVENTOR(S) | : Yeh et al. |

Page 1 of 1

It is certified that error appears in the above-identified patent and that said Letters Patent is hereby corrected as shown below:

In the Specification

Column 1, Line 14, please insert, (approx.):
--NOTICE OF GOVERNMENT-SPONSORED RESEARCH
This invention was made with government support RD83556901 awarded by the Environmental Protection Agency. The Government has certain rights in the invention.--

Signed and Sealed this
Twentieth Day of August, 2019

Andrei Iancu
*Director of the United States Patent and Trademark Office*